United States Patent

Goodman et al.

Patent Number: 5,380,589
Date of Patent: Jan. 10, 1995

[54] BIOTEXTURED SURFACES

[75] Inventors: Steven L. Goodman, Madison; Ralph M. Albrecht, Belleville, both of Wis.

[73] Assignee: Wisconsin Alumni Research Foundation, Madison, Wis.

[21] Appl. No.: 49,209

[22] Filed: Apr. 19, 1993

[51] Int. Cl.⁶ .......................... B29D 23/22; B32B 1/08
[52] U.S. Cl. ........................ 428/36.92; 428/35.7; 428/39; 428/103
[58] Field of Search .............. 428/35.7, 36.92, 39, 428/103, 188; 138/177

[56] References Cited

PUBLICATIONS

D. Steeber, et al., 1 Scanning Microscopy 831–839 (1987).
K. Hodde, et al., 4 Scanning Microscopy 693–704 (1990).
D. Steeber, et al., 313–329 in Scanning Electron Microscopy Of Vascular Casts (1992).
D. Bjorling, et al., 28 J. Pham. Tox. Meth. 149–157 (1992).
R. Whalen, 34 Trans. Am. Soc. Artif. Intern. Organs 887–892 (1988).
S. Williams, et al., 4 Scanning Microscopy 181–189 (1990).
J. Schmidt, et al., 12 Biomaterials 385–390 (1991).
D. Stenger, et al., 114 J. Am. Chem. Soc. 8435–8442 (1992).
I. Amato, 258 Science 1084 (1992).
B. Brune, USA Today (Mar. 1, 1993).
F. Lefebvre, et al., 13 Biomater. 28–33 (1992).
L. Bordenave, et al., 13 Biomater. 439–446 (1992).
S. Taylor, et al., 17 J. Biomed. Mat. Res. 205–227 (1983).
C. Weinberg, et al., 231 Science 397–400 (1986).
E. Einarsson, et al., Scanning Electron Microscopy I 273–278 (1984).
D. Ingbar, et al., 109 J. Cell. Biol. 317–330 (1989).
S. Goodman, et al., in Colloidal Gold; Principles, Methods, And Applications, vol. 3, 369–409 (1991).
S. Williams, et al., 26 J. Biomed. Mat. Res. 103–117 (1992).

Primary Examiner—Charles R. Nold
Attorney, Agent, or Firm—Quarles & Brady

[57] ABSTRACT

Synthetic biotextured surfaces and methods to produce the surface are disclosed. The surfaces mimic the topography of a surface of a naturally occurring sub-endothelial or sub-epithelial extracellular matrix. This is achieved by removing a cell layer from the naturally occurring extracellular matrix substrate, covering the extracellular matrix with a casting material, and allowing the casting material to harden. One then removes extracellular matrix from the casting material to uncover a negative core, and then uses the negative core to cast the replica material. By removing the negative core from the replica material one then creates the synthetic surface.

4 Claims, 2 Drawing Sheets

BIOTEXTURED SURFACES

FIELD OF THE INVENTION

This invention generally relates to biotextured surfaces having medical and biotechnical applications. More specifically, it relates to articles having synthetic surfaces that mimic sub-endothelial or sub-epithelial surfaces, and methods to produce these synthetic surfaces.

DESCRIPTION OF THE ART

There have been various attempts to implant vascular grafts, heart valves, and other non-vascular devices into the human body. However, vascular implants often lead to thrombi development and/or unstable flow patterns, while excessive scarring often occurs on device surfaces.

To reduce these problems, vascular grafts and other implantable materials have been provided with textured surfaces. For example, fabrics, polymerics, metals, and ceramics have been provided with pillar, groove, dimple, and other relatively simple textures. These surfaces have, to some extent, helped to reduce the above problems by enhancing cellular adhesion. However, further improvement is still desired.

SUMMARY OF THE INVENTION

In one aspect, the invention provides an article having an artificial surface which mimics a portion of a peripheral surface of a mammalian sub-endothelial or sub-epithelial extracellular matrix ("ECM"). The artificially formed surface can be made of plastic, the article can be a conduit usable for a vascular graft, and the article can be formed by using a molding core that has a surface that is an inverse representation of the peripheral surface of the matrix.

In another aspect, the invention provides a method of creating an article with a textured surface. One exposes a surface of a sub-endothelial or sub-epithelial extracellular matrix by removing a cell layer therefrom, then covers the matrix surface with a casting material and allows the casting material to harden against the surface. One then removes the extracellular matrix from the casting material so as to uncover a negative cast of the matrix surface. One then covers the negative cast with a replica material and allows the replica material to harden against the cast. Thereafter, one removes the negative cast from the replica material so as to uncover a textured surface that mimics the exposed matrix surface.

An important aspect of the invention is the discovery that when the periphery of a sub layer is mimicked and the resultant exposed to a seeding or sodding supply of a patient's own endothelial cells, the resulting artificial sub-layers can become coated, in vivo, with natural cells to form a "pseudo natural" surface. See S. Williams et al., 26 J. Biomed. Mat. Res. 103–117 (1992) (general techniques for sodding a graft). The disclosure of this article, and of all other articles referred to herein, are incorporated by reference as if fully set forth herein. Surprisingly, the new layer will act substantially like that of the naturally occurring luminal layer.

Another aspect of the invention is the discovery of how during molding the pressure of the casting fluid can be controlled so as to permit accurate replicas to be made. Pressures are controlled during casting so as to simulate in vivo conditions at the time the core hardens.

Yet another aspect of the invention is the discovery that the naturally occurring sub-layer can be accessed in a way that permits accurate and functional replicas of the sub-layer to be made.

The objects of the invention therefore include providing:

(a) articles with synthetic surfaces of the above kind which can support and sustain endothelial or epithelial cell growth; and (b) methods for producing such articles.

The foregoing and other objects and advantages of the invention will appear from the following description. In the description reference is made to the accompanying drawings which form a part hereof, and in which there is shown by way of illustration preferred embodiments of the invention. These embodiments do not represent the full scope of the invention. Rather, reference should be made to the claims herein for interpreting the scope of the invention.

DETAILED DESCRIPTION OF THE PREFERRED EMBODIMENTS

Overview

Figure 1:
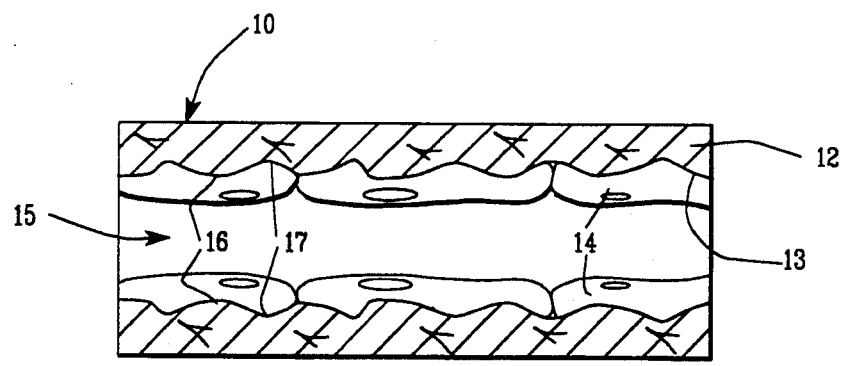
FIG. 1 is a schematic view, in partial cross section, of an artery.

A naturally occurring cylindrical vessel (e.g. an artery) 10 consists primarily of a cylindrical sub-endothelial extracellular matrix 12 (ECM) having a peripheral surface 13 which supports endothelial cells 14. Cells 14 and the ECM 12 together define a vessel passageway 15. The surface 13 of the ECM 12 has a plurality of highly complex surfaces which are schematically represented by hills and valleys (16 and 17). The endothelial cells 14 adhere to the naturally occurring surfaces of the ECM 12. The present invention generates a synthetic ECM 12' with a surface 13' that precisely mimics the peripheral surface of ECM 12.

I. Tissue Preparation

To produce an artificial ECM 12', an artery or vein 10 of the required size and morphology is obtained from an appropriate anatomical location and preferably from a mammalian species. Examples are horse placenta and rabbit thoracic aorta, porcine iliac, femoral, and umbilicus, and human placenta and umbilicus. The vessel 10 is excised and stored in a suitable physiological buffer solution such as phosphate buffered saline (PBS) (154 mM NaCl, 16 mM NaH$_2$PO$_4$, pH 7.3) with 1,000 units/liter porcine Heparin, and placed on ice for transport.

Tissues are then used within 1-2 hours. To relax and smooth arterial muscles, 3 mM sodium nitrate, in fresh PBS, can be added to the bathing media.

Figure 2:
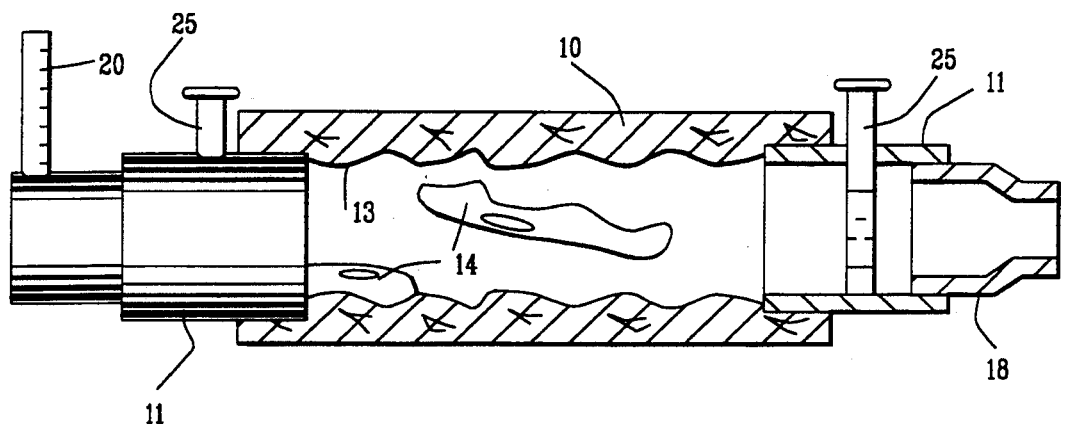
FIG. 2 is a similar view, albeit depicting how an internal luminal cell layer of the artery can be removed.

Referring to FIG. 2, cannula 11 are used at both proximal and distal ends to cannulate the vessel 10. A syringe 18 is used at a proximal end to gently fill and distend the vessel 10 to its in vivo state, with PBS solution. Any collateral vessels are ligated, as required. To insure that the physiological degree of distention is closely monitored, a water column manometer 20 is attached to the distal cannula 11. The preferred physiological pressure is the naturally occurring pressure in the in vivo operating vessel 10. For most arteries, a pressure of 80 mm Hg ($\approx$43 cm water) approximates the mean actual blood pressure. For veins, a lower pressure is used. Following distention, any blood remaining in the vessel 10 is removed by gentle irrigation with PBS.

To expose the underlying ECM without causing damage to its structure, the luminal vessel surface 13 is gently denuded of its endothelial cell lining 14 by bubbling air through the distended vessel 10 for 1-2 minutes, followed by a gentle flushing through with PBS. The bubbling and flushing process is then repeated to insure the complete removal of adherent and nonadherent endothelial cells 14. See generally D. Bjorling et al., 28 J. Pharm Tox. Meth 149-157 (1992).

The removal of endothelial cells 14 is monitored by observing turbidity in the flow stream at the distal end of the surface 10. The quality of endothelial cell 14 removal, and the extent of any damage to the ECM 12, is determined by examination with high resolution three dimensional (stereo) scanning electronmicroscopy (3-D SEM).

In addition to air-denuding, other methods may also be used to remove endothelial cells and epithelial cells. These include enzyme treatments such as trypsin, detergents such as saponin, balloon angioplasty, catheters, mechanical rubbing protocols, antagonists or cytotoxic agents for adhesive cells, antagonists to cell adhesion receptors such as ARG-GLY-ASP peptides to inhibit integrin receptors, and/or specific antibodies (or fragments thereof) to adhesion receptors.

II. Casting

Figure 3:
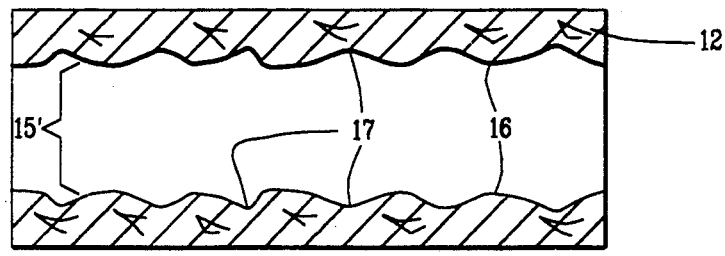
FIG. 3 is a similar view, with the luminal cell layer removed.

Referring next to FIG. 3, after the endothelial cells 14 are denuded and removed from the luminal surface 13, the ECM 12 is left behind. The matrix surfaces (16 and 17) are completely exposed, and define an enlarged vessel passageway 15'.

Next, an inverse or negative "core" replica of the ECM 12' is created with a 1:1 volume mixture of methylmethacrylate monomer and Mercox CL-2B resin 22 (Dainippon Ink and Chemicals, Tokyo). It is injected through the syringe 18 and completely displaces the PBS media within the enlarged passageway 15'. After the passageway 15' has been filled with the resin 22, pressure within the passageway 15' is adjusted and continuously monitored with the water column manometer 20 and brought to the appropriate physiological level.

The catalyst (benzoyl peroxide) is pre-mixed with the methylmethacrylate (at 0.16 g/ml), which is then mixed with the Mercox to a final 0.08 g/ml concentration prior to injection. The pre-mixed catalyst is added through the syringe 18 to the resin 22 to begin the polymerization process. Polymerization does not commence for at least five minutes, thereby providing ample time to fill the vessel. Stopcocks 25 at both the proximate and distal ends of the vessel passageway 15' are closed and monitored in order to maintain steady pressure until the resin 22 has fully polymerized (overnight or as little as 1-2 hours). At all times throughout tissue preparation and casting, vessels 10 are maintained in a room temperature PBS bath. The bath also minimizes heating during polymerization. When filling large volumes, the heat of polymerization may require further chilling of the tissue bath.

Various other materials may be used for the core. These include variant methacrylate formulations and other commercial casting polymers (e.g. Batson's resin, Polysciences Inc., Warrington, Pa.), as well as other polymers which can be polymerized in place. Other materials that may also be used include materials which are infused as melts and then harden in place (some polymers and metal alloys), and materials which harden by other chemical means (such as some ceramics). The qualities necessary for good replication include low viscosity when injected in, minimal shrinkage, ability to replicate fine surface details, and minimal damage to biological tissues.

In applications where the inverse core must be destroyed to be removed (such as for the replication of organs, tissues and other complex luminal structures), casting materials which are easily removed by solvation, chemical degradation, melting and/or other processes are preferred. Low melting temperature metal alloys offer many of these features.

III. Tissue Removal

Figure 4:
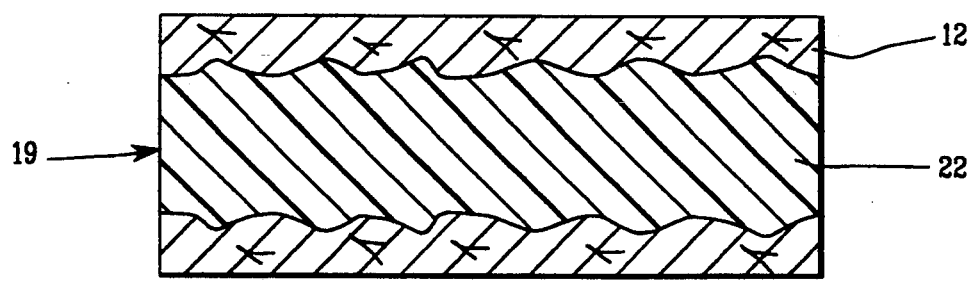
FIG. 4 is a similar view, albeit with a casting material inserted in the FIG. 3 artery so as to form a casting core.

Referring to FIG. 4, to expose the core 19, the ECM and surrounding tissue 12 is preferably removed by a maceration process. Rapid ECM 12 removal can be achieved by placing the ECM 12 in 5% KOH at 40° C. for 1-2 days, followed by 2-3 days in 1% KOH. Each day the hydroxide bath is changed. Following complete ECM and tissue 12 removal, the core 19 is thoroughly rinsed in distilled water, followed by 100% ethanol, and then air dried from ethanol. At this point, the quality of the negative core 19 may be assessed with a 3D stereo SEM.

Figure 5:
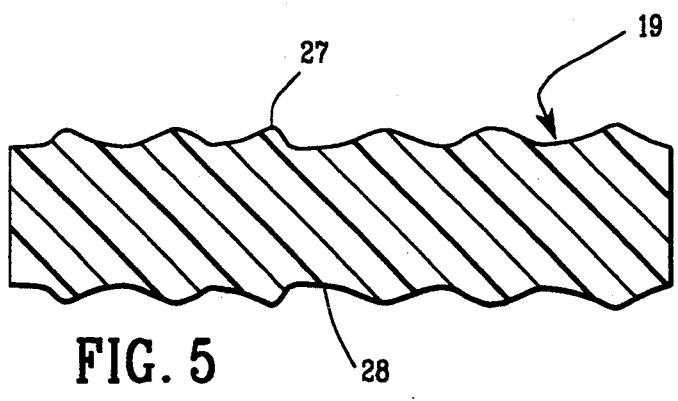
FIG. 5 is a view of the FIG. 4 core, albeit after the artery has been removed by maceration.

Referring to FIG. 5, the resulting core 19 will be the inverse of the original ECM 12. Each hill 27 of the core 19 represents a valley 17 on the ECM 12, and each valley 28 on the core 19 represents a hill 16 on the ECM 12.

With other casting materials, different corrosion agents may be required if caustic conditions (such as NaOH or KOH) damage the inverse ECM replica. Such other corrosion means include detergents, enzymes, and biodegradation with bacterial, cellular, or organism cultures. In addition, with casts of other materials, and with casts of especially delicate structures, air drying from ethanol may not sufficiently minimize surface tension drying forces. Other techniques, such as air drying from other low surface tension media, drying from the critical point, and/or freeze drying, may be required. The drying step may also be eliminated with some protocols described in Section IV, below.

IV. Replicating The Matrix

Figure 6:
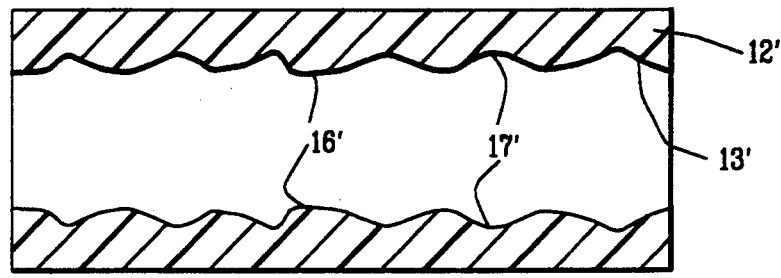
FIG. 6 is a view similar to FIG. 3, albeit of a synthetic artery that has been formed by using the FIG. 5 core.

Referring to FIGS. 5 and 6, a synthetic ECM 12' is prepared by using the core 19 as a molding core to create synthetic biotextured surfaces (e.g. 12'). In the present example, solution grade Biomer (Ethicon Inc., Somerville, N.J.) is chosen. It is a polyurethane biomaterial. The synthetic ECM 12' is prepared by dipping the core 19 a minimum of ten times into a 4% solution (weight/volume) of Biomer in dimethyl acetamide. This provides a polyurethane film thickness of 10 to 15

μm which is suitable for cellular adhesion assays. Thicker conduits can be prepared with more dips.

The core 19 is then removed by solvation in acetone to expose a synthetic ECM 12' with a luminal replica surface 13' which has precisely the same hill and valley (16' and 17') configuration which was originally present on the luminal surface 13 of the naturally occurring ECM 12. While "Biomer" was used in our initial studies, other polyurethanes may also be used. These include polyether polyurethanes, polyester polyurethanes, other biostable polyurethanes, and polyurethanes which incorporate special chemistries designed to influence cell behavior (e.g. materials which incorporate or are grafted with bioactive chemical groups).

Other materials such as porous polymers, materials which are designed to degrade to be replaced by the body's tissues, and materials with surface chemical modifications are also possible. This includes materials of biological origin, as well as synthetic polymers, metals and ceramics. As described, coatings may be applied by virtually any process, including casting from solvent by dip, spray and phase inversion casting, as well as plasma deposition.

Porous structures can be formed either during the replication of the core by solvent manipulations (such as phase inversion), or by processing after the replication process. Porosity may also be achieved after replication by selective solvation, ion beam etching, plasma treatment, and other techniques.

Post replication modifications can be used to incorporate bioactive groups (such as adhesion peptides, carbohydrate moieties, anti-thrombotic agents, and anti-bacterial agents), and/or to alter surface chemistry through wet chemistry, and/or plasma treatments. Post replication techniques can also be used to modify the geometry of the replica, such as producing or sealing holes, joining, straightening, and curving the replica. For example, when replicas of vascular networks are used to encapsulate cells, the ends of vessels may be sealed to form the capsule by the selective application of solvents, adhesives, or heat (with thermoplastic resins).

Natural biopolymers may be used in the replica, such as collagen, fibronectin, laminin and other ECM proteins, by casting and/or polymerizing these against the negative cast. By the same process, diffusible agents such as growth factors may also be incorporated into the material to optimize cellular behavior on the biotextured surface. These are all intended to be within the definition of "synthetic" or "artificial".

Polymers which are designed to degrade may be used to create a controlled release of such compounds. Degradable materials may also be used to facilitate the replacement of the device's structure by the host's own tissues in an implanted device.

If required, the initial negative cast may be replicated twice in order to prepare the core in a stronger form, thus of sufficient strength for multiple uses as an impression mold. As an alternative, a suitable strong core could create a surface on a flat plate by rolling the core on the plate while the plate is still soft.

By using a suitably solvent resistant negative core, tubular replicas (such as vascular grafts) may be removed by swelling the replica material in an appropriate (e.g. Floury) solvent, and then subsequently removing the solvent to restore the tubular replica to its original dimensions. This would permit the negative core to be used repeatedly as a production mandril.

V. Endothelial Cell Growth

Figure 7:
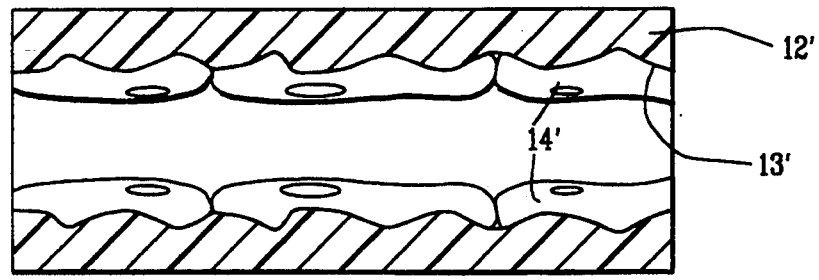
FIG. 7 is a view similar to FIG. 1, albeit showing how the FIG. 6 artery, when implanted in a human body after cell seeding, will permit an endothelial luminal cell layer to form.

Referring to FIG. 7, bovine aortic endothelial cells 14' (BAECs), cultured in Dulbeccos modified essential media containing 20% fetal bovine serum and 2 mM glutamine, are plated at a density of $4 \times 10^4$ cells/ml onto the textured synthetic surface 13. The endothelial cells 14' are cultured in an 8% $CO_2$ incubator at 37° C. The cells were then allowed to attach and spread for up to four days, and then fixed with 1% glutaraldehyde in HEPES buffer (pH 7.3). Samples were then post-fixed in 0.05% $OsO_4$ in HEPES, dehydrated in serial ethanols, dried and ion beam Pt coated for low voltage SEM scanning.

VI. Results

Three dimensional SEM observation of the ECM 12 exposed by the air denuding protocol showed that virtually 100% of endothelial cells 14 were removed, and there was no apparent damage to the ECM 12. For comparison, vessels 10 denuded by gentle rubbing with cotton swabs show that rubbing does not remove all endothelial cells 14 and can cause tearing of the extracellular matrix 12.

Three dimensional SEM imaging of the core 19 shows excellent replication of the ECM 12. Faithfully replicated are overall vessel shape (centimeters) as well as microscopic features including the complex fiber matrixes, pores, clefts and nuclei-sized depressions found in the naturally occurring ECM 12, including macromolecular topographies as small as circa 10 nm.

In other experiments, we have demonstrated accurate methacrylate casts of certain organs and tissues. While the above discussion relates to luminal endothelial systems, with other geometries and/or non-vascular tissues, the process would entail a similar denuding step. Then a tubular "core" for an "outer" surface would be formed between an outer removable tube and the sub-extracellular matrix. The core would then have the replica formed inside of it. Examples include replication of the sub-epithelial ECM of corneas and skin, and sub-endothelial ECM of heart valves.

Our tests have shown that the ECM-textured surface promotes more rapid initial cell spreading of BAECs than did an untextured control surface. Cell seeding and attachment progresses more rapidly on this substrate. Additionally, the more rounded appearance of BAECs at 4 day confluent culture (and consequently smaller spread area in confluent culture) indicated that the final result is a structure much more like that observed in native arteries than observed on smooth control surfaces.

The strength of cell adhesion should also be increased due to the large area of surface contact on the highly textured surface, and since its topography permits mechanical interlocking. Additionally, since the texture replicates that of the ECM, the surface should also have the benefit of facilitating phenotypic differentiation of cells.

Our biotextured materials will find utility in many biomedical and biotechnological applications. Applications inside the body include implanted medical devices in which controlled cell adhesion is desired (e.g. vascular grafts, prosthetic cardiac valves, artificial corneas, artificial skin, orthopedic and dental prosthetics, implanted drug delivery devices, biosensors, encapsulated cell transplants, and organoids) and on the surface of implanted device enclosures such as pacemaker enclosures. Biotechnological applications outside the body include laboratory culture dishes and bioreactors for adhesion dependent cell cultures.

By employing the technology with whole organs and tissues, rather than isolated blood vessels, the vascular structure (or other luminal and non-luminal structures) of entire tissues may also be replicated. Due to the high density and surface area of such organs and tissues, these structures should be useful for culturing extremely high numbers of cells per unit volume within a device with an appropriate (evolution optimized) geometry for excellent delivery and transport of nutrients, wastes and desired products to and from cultured cells.

Replicas of some vascular capillary networks may also be useful as containers for therapeutic cell transplants (such as pancreatic islets and other cells), even without being incorporated into a vascular circulation. Since (replicas of) many vascular tissues have extremely high surface to volume ratios, with luminal diameters which are at most a few cell diameters across, these replicas can encapsulate extremely high numbers of cells in a small volume, with the maximum surface area for diffusion into and out of the device. Such replicates of tissue or organ architecture may also be used in biotechnology (in bioreactors) and in medicine, as the 3-dimensional basis of artificial organs, organoids, and drug delivery devices.

We claim:

1. An article having an artificial surface in the form of a casting which essentially replicates a portion of a peripheral surface of a mammalian sub-endothelial extracellular matrix or sub-epithelial extracellular matrix, wherein the article was formed by using a molding core that has a surface that is an inverse representation of the peripheral surface.

2. The article of claim 1, wherein said matrix is a sub-endothelial extracellular matrix.

3. The article of claim 1, wherein the artificial surface is made of plastic.

4. The article of claim 1, wherein the article is a conduit.

* * * * *